US011969376B2

(12) United States Patent
Dellanno

(10) Patent No.: US 11,969,376 B2
(45) Date of Patent: Apr. 30, 2024

(54) FORWARD HEAD POSTURE CORRECTION COLLAR

(71) Applicant: Ronald P. Dellanno, Bloomfield, NJ (US)

(72) Inventor: Ronald P. Dellanno, Bloomfield, NJ (US)

(73) Assignee: Ronald P. Dellanno, Bloomfield, NJ (US)

( * ) Notice: Subject to any disclaimer, the term of this patent is extended or adjusted under 35 U.S.C. 154(b) by 252 days.

(21) Appl. No.: 16/362,098

(22) Filed: Mar. 22, 2019

(65) Prior Publication Data

US 2020/0015994 A1    Jan. 16, 2020

Related U.S. Application Data

(60) Provisional application No. 62/646,523, filed on Mar. 22, 2018.

(51) Int. Cl.
*A61F 5/058*    (2006.01)
*A61F 5/055*    (2006.01)

(52) U.S. Cl.
CPC .......... *A61F 5/05816* (2013.01); *A61F 5/055* (2013.01)

(58) Field of Classification Search
CPC .. A61F 5/048; A61F 5/05; A61F 5/055; A61F 5/05816; A61F 5/05883; A61F 5/05891; A61F 5/32; A61F 5/34; A61F 5/3707; A61F 2250/0004; A63B 71/1291; A61H 1/008; A61H 1/0292; A61H 1/0296
USPC ........... 602/13, 17, 18, 19, 32; 128/857, 869
See application file for complete search history.

(56) References Cited

U.S. PATENT DOCUMENTS

| 2,791,999 | A | * | 5/1957 | Bustamante | ............ A61F 5/055 601/39 |
| 4,643,174 | A | | 2/1987 | Horiuchi | |
| 5,575,763 | A | | 11/1996 | Nagata | |
| 7,951,102 | B2 | | 5/2011 | Gefen et al. | |
| 8,764,693 | B1 | | 7/2014 | Graham | |
| 9,913,746 | B2 | * | 3/2018 | Martin | .................... A61F 5/055 |

(Continued)

FOREIGN PATENT DOCUMENTS

CN    104146848 A  *  11/2014    ............... A61H 1/02

OTHER PUBLICATIONS

Rice University, Rice University Students Create Better Cervical Collar, Apr. 9, 2012, Youtube, https://www.youtube.com/watch?v=J8wnuXQTm-k&feature=emb_logo (Year: 2012).*

*Primary Examiner* — Alireza Nia
*Assistant Examiner* — Michael Milo
(74) *Attorney, Agent, or Firm* — G. Glennon Troublefield

(57) ABSTRACT

A forward head position correction collar is provided having first assembly mounted around the shoulder and neck portions of a wearer. A second assembly is movably connected to the first assembly. The second assembly includes a pair of opposed first and second adjustment assemblies that are used to position first and second cheek engagement pieces on the face of the wearer. The first and second cheek engagement pieces are joined to one side of a chin-mastoid piece that can be adjusted relative to the wearer. Preferably, a lordosis correction fulcrum assembly is formed within the first assembly to selectively and incrementally engage the rear of the wearer to apply corrective forces against the cervical area of the neck.

7 Claims, 19 Drawing Sheets

(56) References Cited

U.S. PATENT DOCUMENTS

| | | | |
|---|---|---|---|
| 2007/0079832 A1 | 4/2007 | Baldauf et al. | |
| 2007/0270728 A1* | 11/2007 | Chao | A61F 5/055 602/18 |
| 2009/0149788 A1* | 6/2009 | Dellanno | A61F 5/055 602/18 |
| 2009/0247918 A1 | 10/2009 | Patrone | |
| 2010/0298748 A1* | 11/2010 | Rosenfeld | A61F 5/055 602/17 |
| 2015/0245940 A1* | 9/2015 | Hardcastle | A63B 21/4025 602/18 |
| 2015/0328038 A1 | 11/2015 | Rosenfeld et al. | |

* cited by examiner

FORWARD HEAD POSTURE CORRECTION COLLAR

This application claims priority based on provisional application Ser. No. 62/646,523, filed Mar. 22, 2018, the contents of which are incorporated by reference in their entirety. This invention relates generally to orthopedic correction devices and apparatus, and more specifically relates to a forward head position correction collar.

FIELD OF THE INVENTION

Background of the Invention

Forward head positioning is an increasingly observed malady in our society. As is well known to orthopedists, chiropractors and other medical practitioners the human head in its normal position should sit in a direct fashion on the neck and shoulders. Partly because of certain increasing habits in our society the head can become displaced to a posture where instead of sitting directly on the neck and shoulders, is displaced forward of that normal position to what is called a "forward head posture" (or "FHP"). FHP is identifiable when the position of the ear is forward when compared to the shoulder, as opposed to being posited directly over it. FHP has become so widespread that it may already constitute a health hazard having the ramifications of a pandemic, since when left untreated FHP can develop degenerative and disabling joint diseases affecting countless numbers of people.

There are numerous reasons why FHP is becoming such a more common problem. For example, vastly increased use of computer screens accustoms the operator to move and maintain the head (and ears) in the undesirable forward head posture. The problem is exacerbated in children and young adults by long hours devoted to video games, not to mention conventional television watching. Yet another source believed to be responsible for the malady particularly in children, is the present custom of children carrying extremely heavy backpacks to and from school. The weight of such backpacks is so high as to require head placement in a forward position to balance the load, which results in the increasing observation of forward head posture in both children and young adults. As another example, FHP occurs in athletes playing contact sports, such as football or soccer, in which a given player's head will move involuntarily in an unplanned direction. In football, it is known that a player's head will moved in several directions when the player is tackled or blocked. In that instance, the head will move in a direction that causes stress on the spine and the head translates forward of the shoulders. The same type of movement may be experienced when a given play is using his or her head during soccer to hit the soccer ball.

Basic damage resulting from forward head posture (FHP) arises because the upper cervical portion of the spine can become chronically misaligned. The head will translate forward of the shoulders. Every inch the head moves forward of the shoulders dramatically adds mechanical weight loads to the neck. For example, an individual with poor posture may have his or her head translate a number of degrees from the anatomically correct position, which is considered zero degrees. In a normal anatomical position, the head aligned forward of the shoulders in the zero degree position, such that the ears are lined up with the center of the shoulder. In that positon, there is about 10-12 lbs. of weight loaded to the neck and cervical spine. When the head moves forward, such that the ears are displaced away from the centerline, there is an increase in the number of pounds imposed on the neck. A 15 degree displacement can create up to 27 lbs. and a 16 degree displacement can impose an additional 60 lbs. on the neck. The forward positioning of the head can pull the spine out of its anatomical alignment, and can add up to thirty pounds of abnormal leverage on the cervical spine and, as a result, can pull the spine out of alignment. Movements in head posture forces muscles in the upper back and neck areas to work harder to keep the head (including chin) properly aligned, as opposed to dropping forwards towards the chest area. It is known by those of ordinary skill in the art that FHP may result in the loss of 30% of vital lung capacity due to the loss of the cervical lordosis. Cervical lordosis is a curvature of the cervical spine or the vertebrae in the neck region. The slight curve present in the cervical vertebrae enables comfortable movement of the neck and supports the weight of the head. The cervical curve allows flexibility between the vertebrae to allow normal head movement. The range of the cervical lordosis is 34 to 44 degrees. When the natural curvature of the spine changes, such that an acceptable cervical lordosis curve is lost or misaligned, problems can arise which present in a number of symptoms, such as neck and back pain, neck stiffness, vertigo and nausea, headaches and tinnitus, high blood pressure, insomnia and fatigue, numbness or tingling sensation in the neck, and other symptoms known in the art.

While the difficulties arising from FHP are certainly well recognized in the healing arts, efforts to correct same by treatment with orthopedic devices and the like have not been successful. Basically such efforts have taken the form of using cervical collars to in some manner immobilize the neck. The objective of these collars, or for that matter of other prior art treatment, has simply been to utilize traction to displace the head from its improper position. Neither these prior art collars, nor to the best of applicant's knowledge any other presently available devices and/or apparatus, are however effective in reversing the damaging effects of FHP.

As used herein, the term "Z-axis" refers to the horizontal axis extending in an anterior-posterior direction with respect to a set of axis positioned at a hypothetical human, where the corresponding vertical axis is referred to as the Y-axis and the horizontal left to right side axis with respect to such human is referred to as the X-axis. Many of the prior art devices that have been used or proposed, while achieving adjustments along the Z-axis are not otherwise concerned with simultaneously improving cervical lordosis. Most cervical collars are designed to immobilize the neck and/or cause axial translation to decompress the cervical spine while causing the cervical spine straightening. This may produce mixed benefits, as ligament impairment cannot improve around a straightened cervical curve, as this is an abnormal alignment, which will ultimately result in permanent arthritic changes to the cervical joints. Ligament rehabilitation requires improvement of joint alignment over time. Most current extension traction therapy designed to improve cervical lordosis is practiced for 20 minutes or less.

Dellanno, U.S. Pat. No. 8,038,635, the disclosure of which is herein incorporated by reference in its entirely, teaches a forward head position correction collar featuring in combination a shoulder collar assembly, a chin-mastoid piece for engaging and positioning the head of a wearer of the collar and a means interconnecting the chin-mastoid piece to the shoulder collar assembly for manually and incrementally adjusting the chin-mastoid piece with respect to the shoulder collar assembly in an anterior/posterior (Z-axis) direction along the Z-axis. It would be desirable to provide an adjustable collar for use in correcting FHP. It would be desirable to provide a forward head position correction collar featuring in combination a shoulder collar assembly, a chin-mastoid piece and a cheek or jaw piece for engaging and positioning the head of a wearer of the collar. It would be preferable to engage and position using force applied to the cheek jaw rather than the chin. One objective of Dellanno is to improve cervical lordosis with a full correction collar over many hours. The present invention is thus relatively comfortable and can be used at work or at home or even during sleeping hours to avoid unhealthy postures that impair the health of an injured neck.

SUMMARY OF THE INVENTION

The present invention features an adjustable forward head posture assembly for use in positioning the head of the wearer to a desired position. The assembly comprises a first member for removably mounting the assembly to the wearer, a second member adjustably secured to the first member, and a third member for engaging the chin of the wearer, which is adjustably secured to the second member. The second member engages a portion of the head of the wearer and is adapted to move relative to the first member for purposes of positioning the third member. The third member engages another portion of the head of the wearer and is adjustably secured to the second member. The adjustable movement of the second member and third member, either individually or in combination, is advantageously used to capture the head of the wearer in a first condition and move the head to a second condition, the second condition being the preferable position of the head relative to the body as desired by the operator of the posture assembly.

Preferably, the forward head position correction collar features a lordosis correction assembly secured to the rear of the collar and engageable with the rear of the wearer for applying corrective forces by enabling increased pressure to be brought against specified vertebrae.

BRIEF DESCRIPTION OF DRAWINGS

The invention is diagrammatically illustrated by way of example in the drawings appended hereto, in which:

FIG. 21 is a schematic cross sectional view depicting sequential changes of the forward head translation and cervical spine configuration of the wearer that can be achieved with the present invention.

FIG. 22 is a schematic cross-sectional view depicting sequential changes that occur in the wearer's head position and spinal configuration when the head translates relative to the shoulders, which causes forward head posture.

DESCRIPTION OF THE PREFERRED EMBODIMENTS

The present invention is a new type of forward head position (FHP) correction collar, which utilizes a mild axial translation with significant corrective Z translation forces for the sagittal planes. The invention provides an orthopedic correction device which can be readily used by a patient suffering from FHP, which can reverse the damaging effects of compressive loading, shear, and neck moments which FHP generates at all seven cervical vertebra of the patient.

In accordance with the present invention a forward head position correction collar is provided which in combination includes a shoulder collar assembly, a chin-mastoid piece, a cheek or jaw piece for engaging and positioning the head of a wearer of the collar, interconnecting means for interconnecting the chin-mastoid piece and/or the cheek or jaw piece to the collar assembly as to enable the chin-mastoid piece and/or the cheek or jaw piece to be manually and preferably incrementally adjustable with respect to the shoulder collar assembly in a Z-direction, to thereby adjust the supported head of the wearer from the forward head position to an increasingly corrected position; and the interconnecting means further being adapted to displace the chin-mastoid piece and/or the cheek or jaw piece in a vertical direction with respect to the shoulder collar assembly simultaneously with and proportional to the incremental adjustment of the chin-mastoid piece and/or the cheek or jaw piece along the Z-axis. The proportional vertical displacement with respect to the z axis displacement for the chin-mastoid support piece and/or the cheek or jaw pieces is that yielded by a point moving at about a 5 to 25° slope, and preferably at a 10 to 25° slope with respect to the horizontal Z-axis.

The FHP correction collar may further include a lordosis correction assembly secured to the rear of the collar. This assembly is engageable with the rear of the wearer for applying corrective force to the upper, middle and/or lower cervical spine. The lordosis correction assembly can also be used to selectively support only one or only several of the seven cervical vertebrae, and thus need not support the entire neck curve. Further, the assembly may by virtue of its fit with a given patient, be able in such instances to support one or more of the upper thoracic vertebrae.

Figure 4:
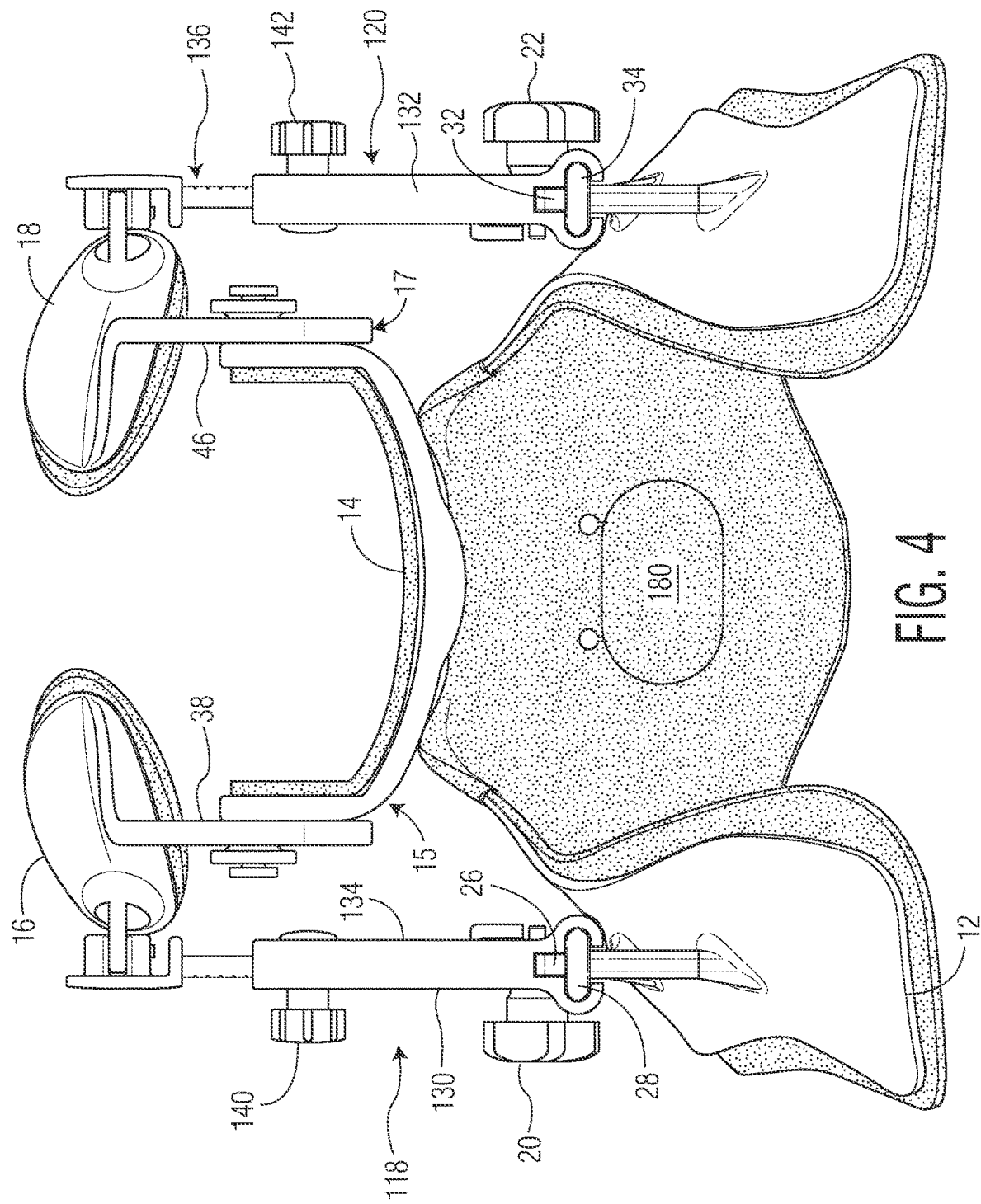
FIG. 4 is a front plan view of the correction collar shown in FIG. 3 further illustrating the bilateral symmetry of the components of the first assembly and the second assembly
Figure 5:
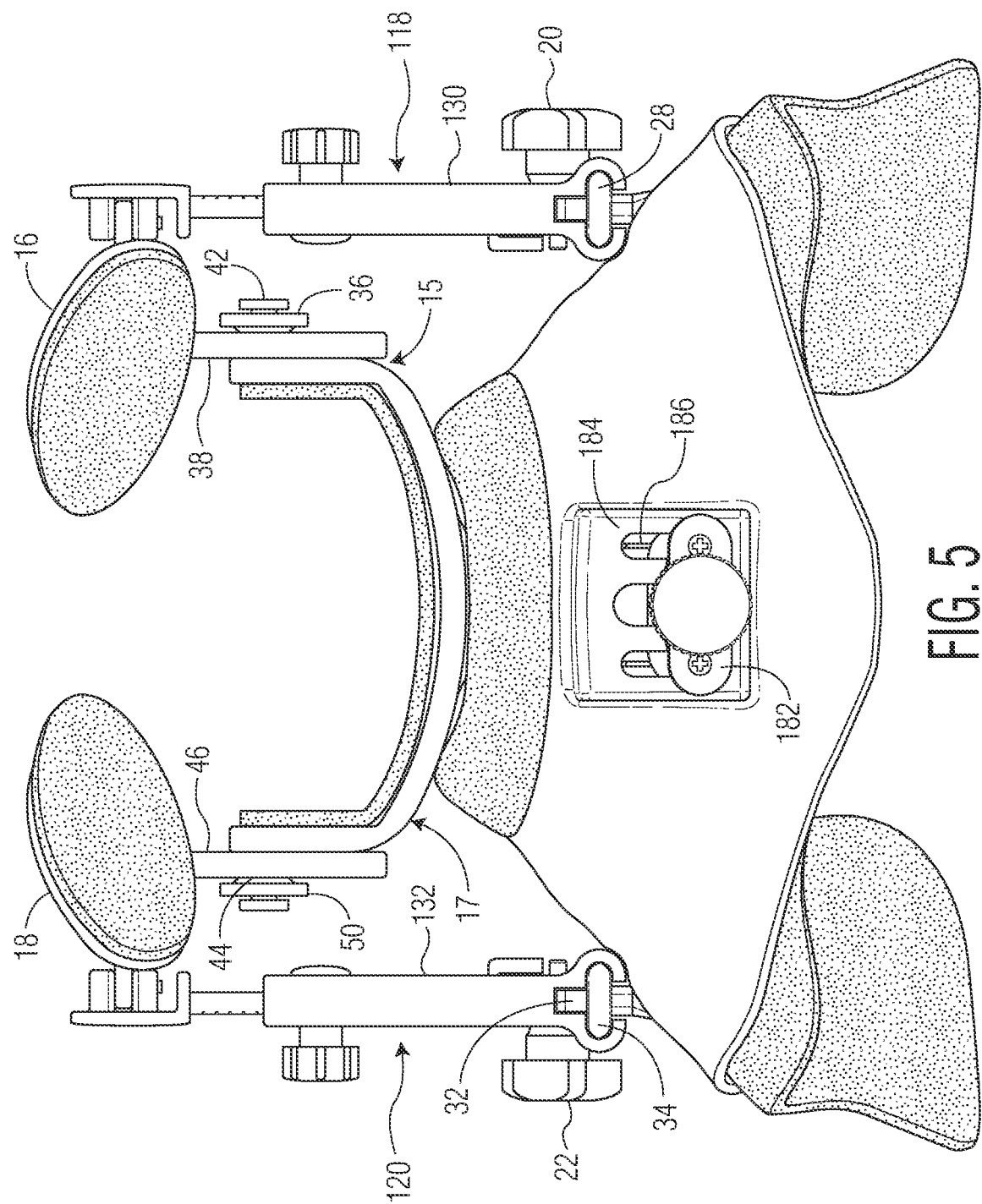
FIG. 5 is a rear plan view of the correction collar shown in FIG. 4.
Figure 6:
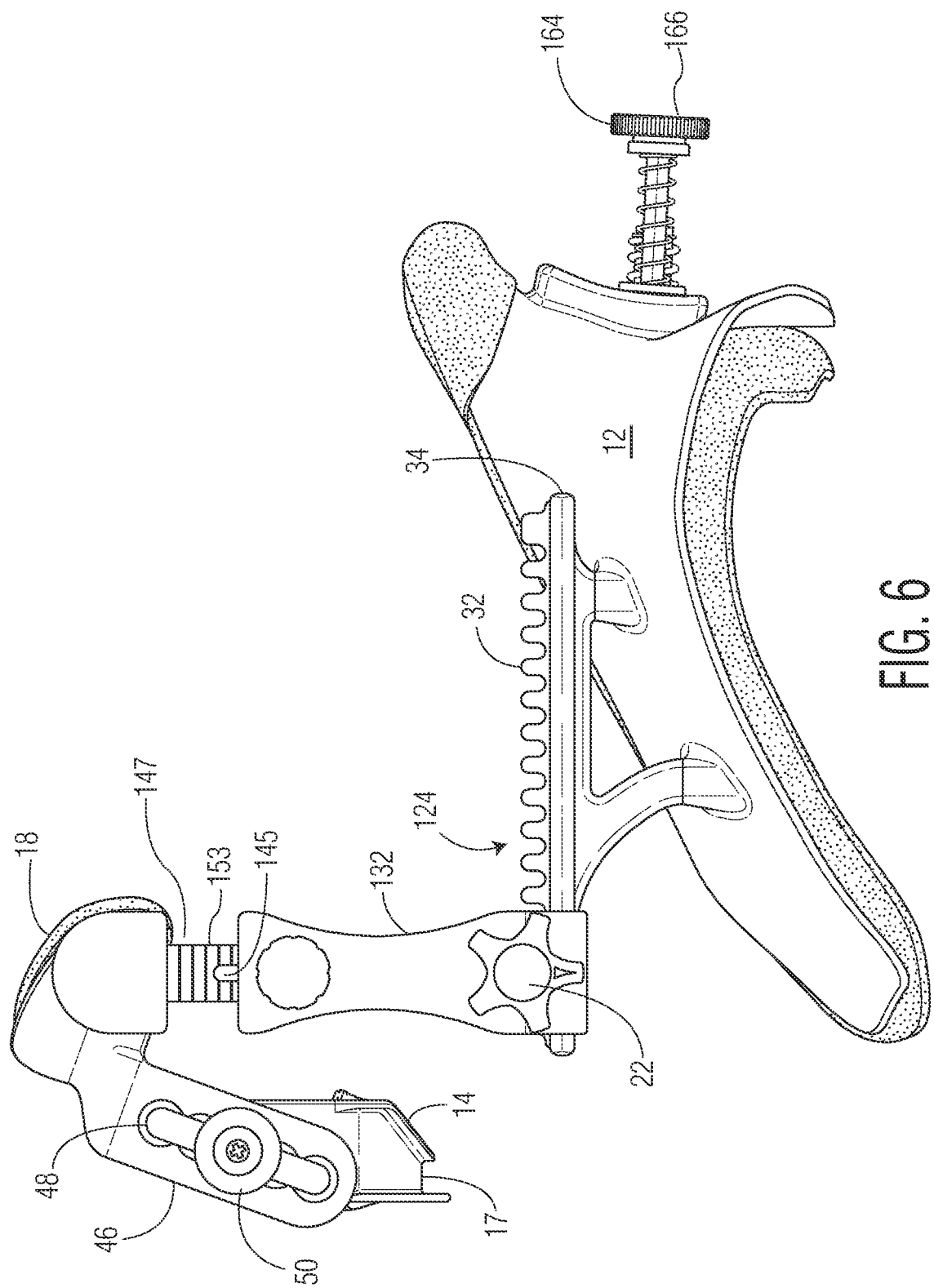
FIG. 6 is an isolated side view of the correction collar shown in FIG. 2, showing the second side of the first assembly and the second assembly, relative to the side view of a one embodiment of the lordosis correction assembly.

It is to be appreciated that the terms "forward" and "back" are often misused when applied to flexion and extension motion of the head. As described herein the reference coordinate system is one wherein the x-axis extends right to left in the frontal plane, the y-axis is the vertical axis, and the z-axis resides in the front to rear sagittal plane. The present invention is concerned with translational movement along the sagittal plane, i.e. in the direction of the z-axis (front to rear). This contrasts to much prior art as exemplified e.g. in such representative prior art as Bonutti U.S. Pat. No. 6,770, 047, which is concerned with rotational movement around the x axis (flexion and extension or looking up or down movement). See, e.g. FIGS. 4 and 5 of Bonutti. The exemplary prior art Bonutti invention is designed to stretch the neck in flexion (negative x direction, see FIG. 4), or in extension (positive x axis direction, looking up, see FIG. 5) The patient can control this motion by an adjustable control knob located at their naval area, whereas in the present invention the control knob is in the neck area and causes a completely different motion. The present invention thus has a neck brace that moves forward (positive z axis) and rearward (negative z axis). There is no flexion or extension motion. The object of the present invention is to correct cervical lordosis breakdown at specific areas and to correct forward head posture. The design of the invention is dictated by the intended motion objectives.

In the views of FIGS. 1, 2, 3, 4, 5, and 6 illustrate a preferred embodiment of the forward head position correction collar 10 assembly. Collar assembly 10 comprises a shoulder collar assembly 12 and a chin-mastoid piece 14, a first cheek or jaw piece 14 and a second cheek or jaw piece 18 for engaging and positioning the head of a wearer when collar 10 is used. The first cheek piece 16 and the second cheek piece 18 are movable with respect to the shoulder collar assembly 12 so as to adjustably reposition the head the wearer of collar assembly 10.

Figure 1:
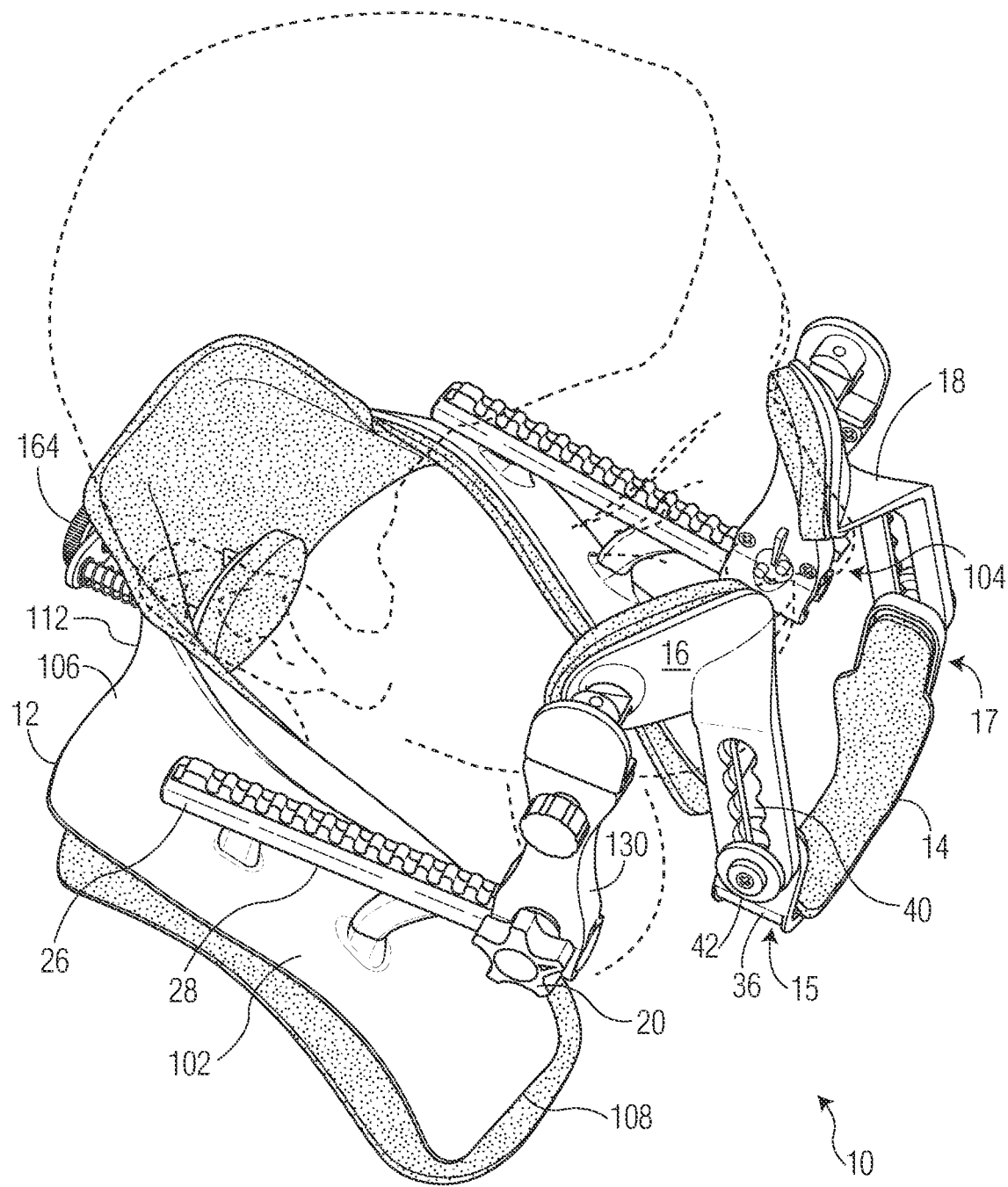
FIG. 1 is a side perspective view of a forward head posture correction collar of in accordance with one embodiment of the present invention in an assembled condition, mounted to the hypothetical head of a wearer shown in phantom.
Figure 2:
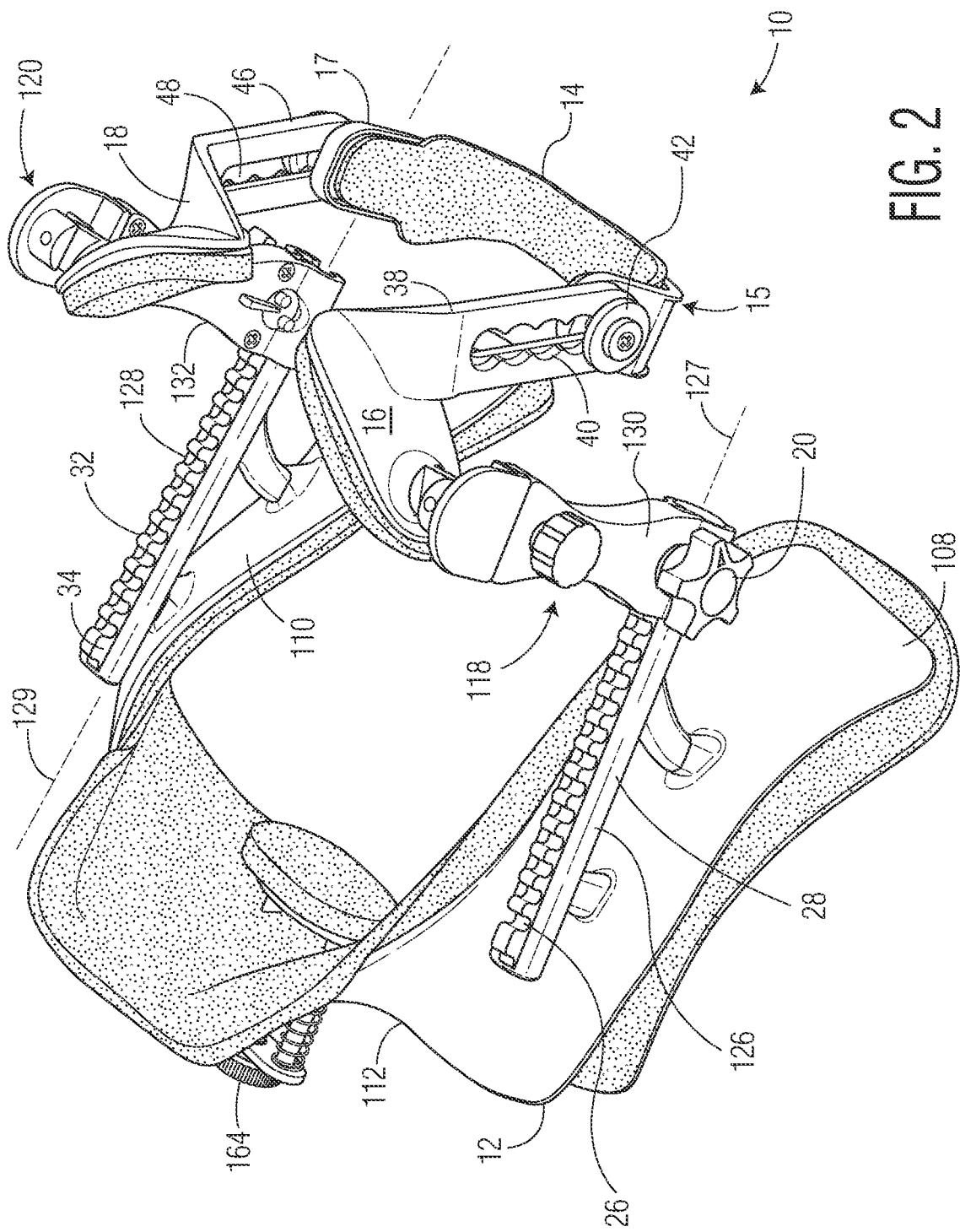
FIG. 2 is a perspective view of the correction collar shown in FIG. 1, without the head of the wearer, showing a first assembly and a second assembly with contain components that are bilaterally symmetrical to each other together with a lordosis correction assembly.
Figure 3:
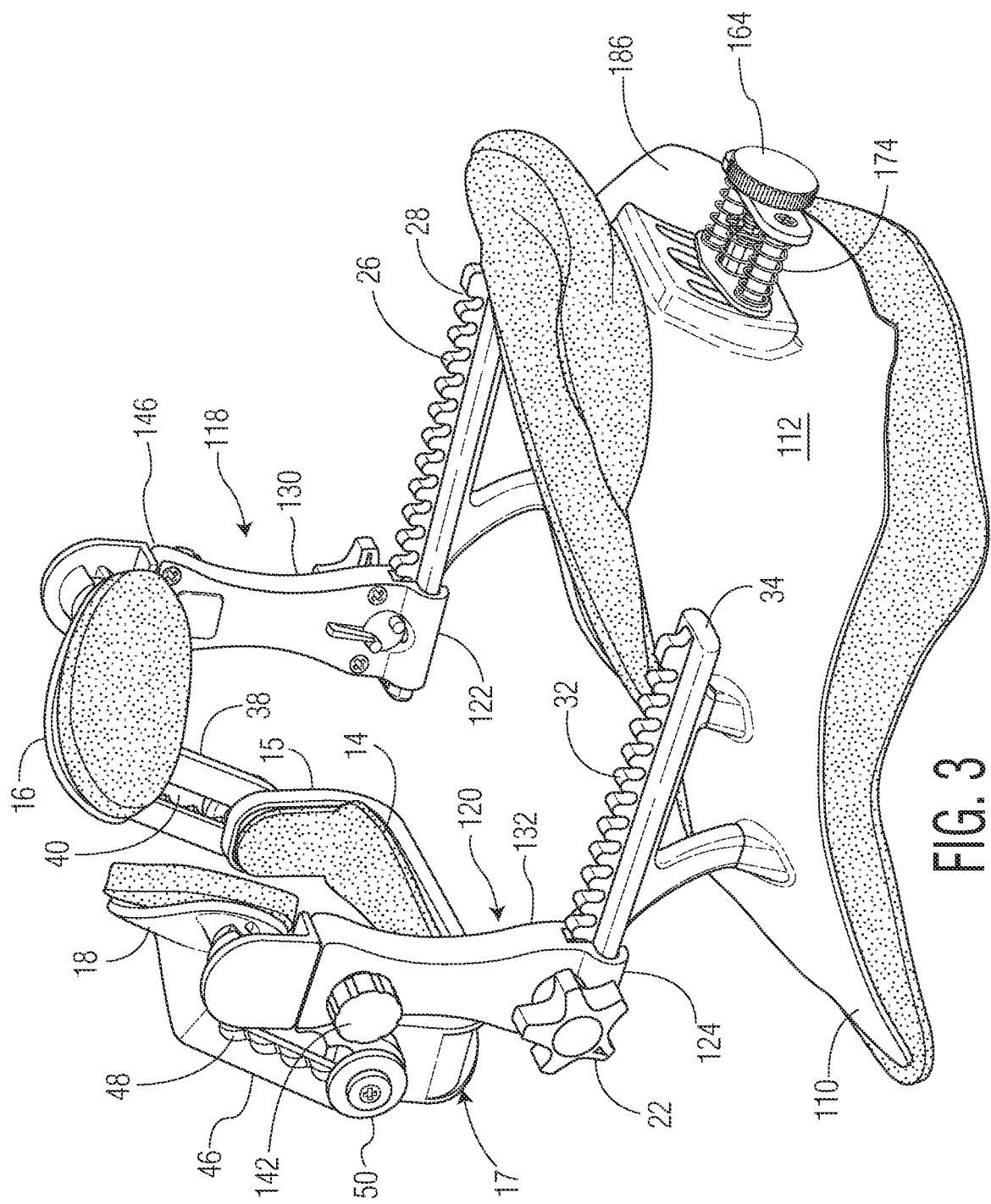
FIG. 3 is a rear perspective view of the correction collar shown in FIG. 2.

The Z-displaced and vertically displaced positions of the chin-mastoid piece 14 and/or the first cheek piece 16 and the second cheek piece 18 with respect to shoulder collar assembly 12 are adjusted by rotation knob 20 on the anatomical right side and by rotation knob 22 on the an anatomical left side of collar assembly 10. Rotation knob 20 is operatively and mechanically connected to rack and pinion type mechanism, defined by pinion gear 24 which is meshed with teeth 26 in track 126 (FIG. 1). Rotation knob 22 is operatively and mechanically connected to a rack and pinion type mechanism, defined by pinion gear 30 which is meshed with teeth 32 of track 128. The rotation of knob 20 and knob 22 is preferably the same during adjustment to preserve maximum symmetry in displacement of the chin-mastoid piece and/or the cheek 18. Such identity in rotation can be controlled manually or by simple interconnects.

Figure 7:
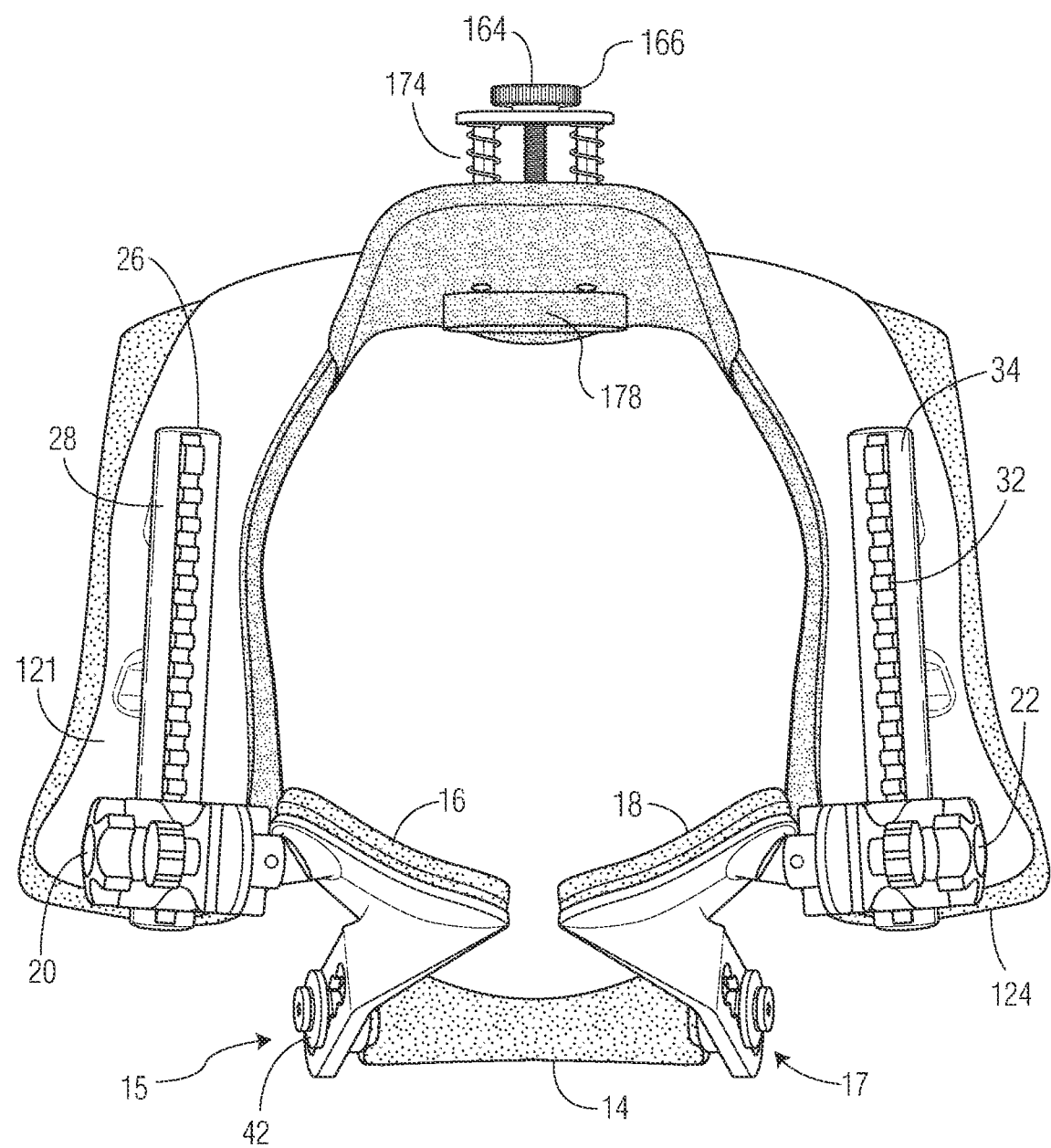
FIG. 7 is a top view of the correction collar shown in FIG. 2, in a first condition having an opening to receive the head of the wearer.

Operation of the collar assembly 10 is better understood by reference to FIGS. 2 through 6. The chin-mastoid piece 14 has a first side 15 and a second side 17. The first side 15 of chin-mastoid piece 14 is joined to the first cheek or jaw piece 16 through a first track 148 (one of a pair, the other being symmetrically secured at the opposed lateral face of piece 14). The form of track 148 may be better seen in FIGS. 6 and 7. The position of the chin-mastoid piece 14 relative to the first cheek or jaw piece piece 16 is controlled by an alignment and locking pin 152 affixed to one side 15 of the chin-mastoid piece 14 and/or the cheek or jaw piece 16 and projecting outwardly. The chin-mastoid piece 14 and/or the cheek or jaw piece 16 are attached via arm 144 having track 148 in which alignment and locking pin 152 releasably engages in slidable fashion within tack 148. The alignment pin 152 is thus seen to engage with the bracket arm 144 and retained by a cap not shown.

Figure 8:
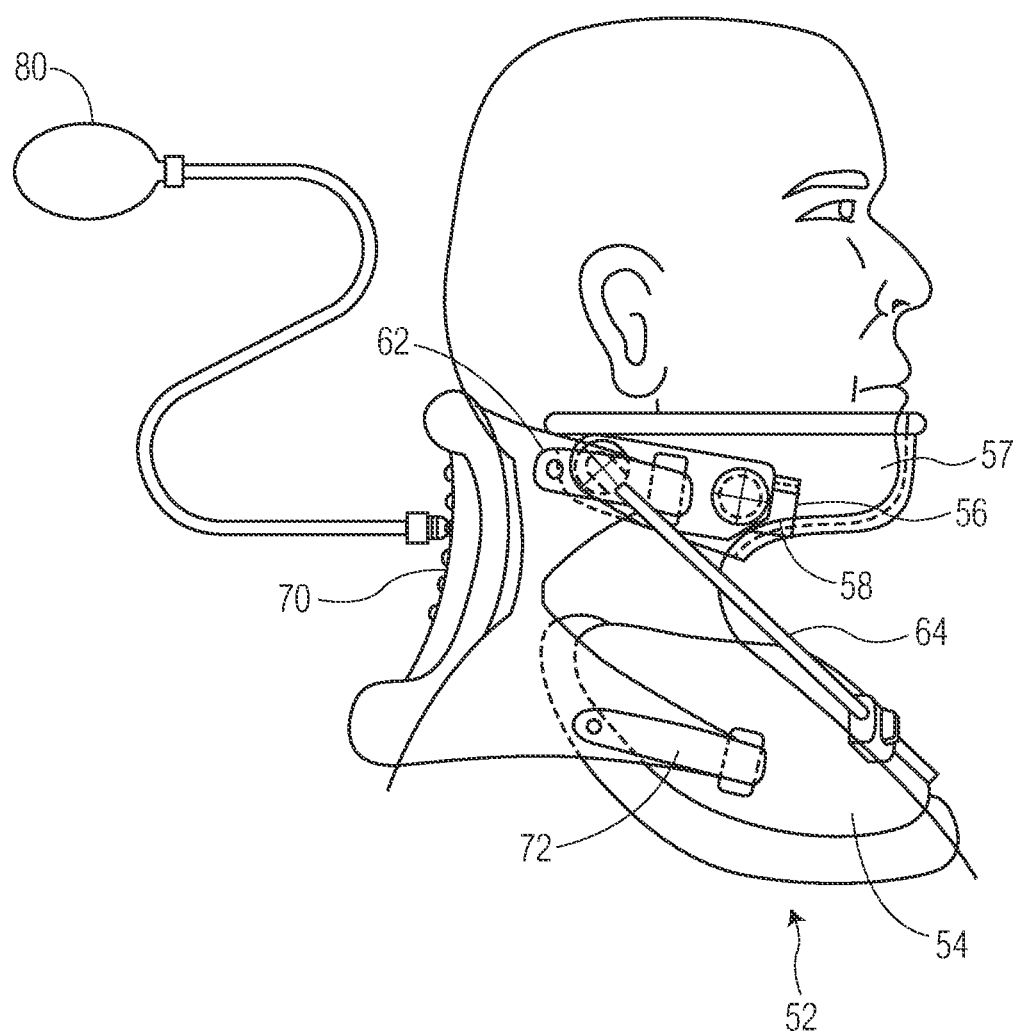
FIG. 8 is a side view of a prior embodiment of the correction collar mounted to the head of a hypothetical wearer with a hypothetical wearer, with a second embodiment of a lordosis correction assembly.

FIG. 8 illustrates a prior embodiment of the forward head position correction collar 52. As shown in FIG. 8, collar 52 comprises a shoulder collar assembly 54 connected on each side of chin-mastoid piece 56 by a pair of support brackets 58 (shown) and 60 (not shown). The chin-mastoid piece 56 includes a cheek or jaw piece 57. Support bracket 68 is connected to chin-mastoid piece 56 by a track 62 and a rod 64. A similar track 66 and rod 68 (each not shown) are present on the opposite side of chin-mastoid piece 56 of collar 52. 1. Each chin-mastoid piece support bracket 58 and 60 is connected to shoulder collar assembly 54 and to a rear lordosis correction assembly 70 (FIG. 8) by the ends of connecting rods 64 and 68 and by strap 72. The chin-mastoid piece 56 is used for engaging and positioning the head of a wearer of the collar 54 by positioning the cheek or jaw piece 57.

Figure 9A:
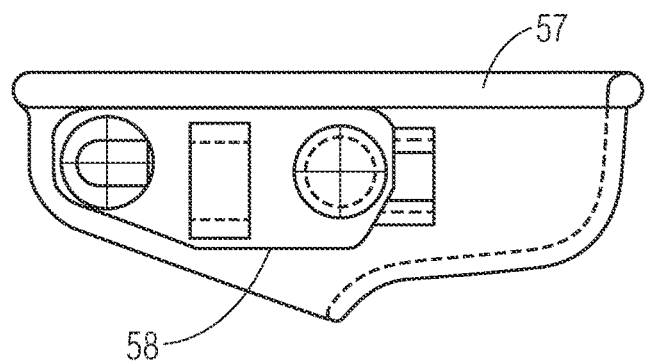
FIGS. 9A and 9B are side and top views of a chin-mastoid piece and chin-mastoid piece support bracket of a second assembly of the correction collar shown in FIG. 8.
Figure 9B:
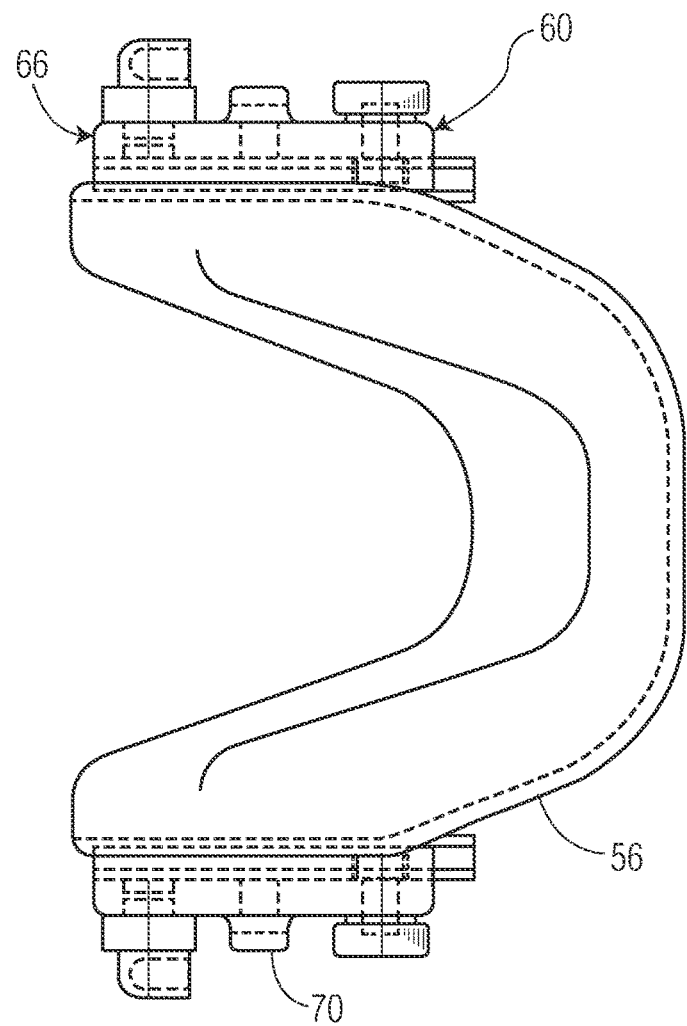
Figure 10A:
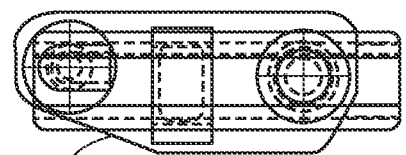
FIGS. 10A, 10B, and IOC are plan, top, and end views of the chin-mastoid piece shown in FIG. 8.
Figure 10B:
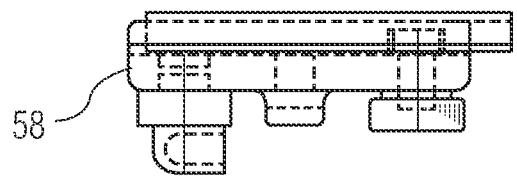
Figure 10C:
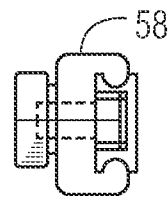
Figure 11:
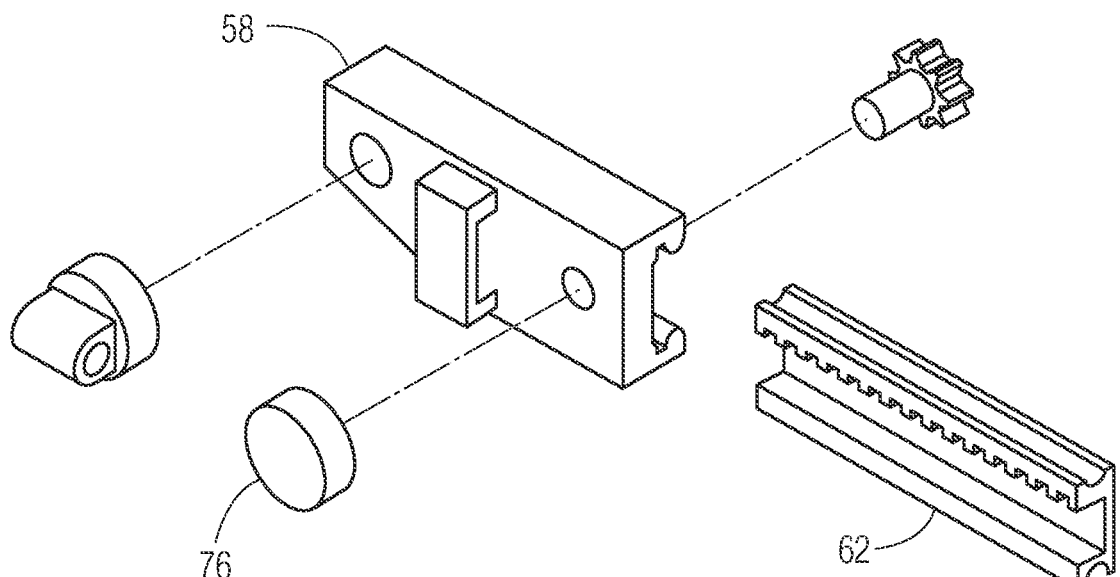
FIG. 11 is an exploded perspective view of the components shown in FIGS. 9A, 9B and 9C.

The interaction between the support bracket 58 and chin-mastoid piece 56 is better seen in FIGS. 9A and 9B. When the adjustment is made the rods 64 are first released by rotating a release means which are locked once the adjustment is complete. The incline for the support track can be in the general range of from about 50 to about with a preferred incline range being from about 10° to about 25° and a typical preferred incline being about 10°.

The cheek or jaw piece 57 engages and positions the head of a wearer of the collar. The cheek or jaw piece 57 may be provided with a pad 74, and is suited for engaging the individual's cheek or jaw at a position lateral to the nose.

Side and top perspective views of the chin-mastoid piece 56 and/or the cheek or jaw piece 57 and associated support bracket 58 appear in FIGS. 9A and 9B. The mastoid bone is located behind the subject's ear and serves as an excellent lever-arm to move the head rearward in correcting the forward head posture. The mastoid bone is part of the head while the chin is part of the jaw, which is connected to the head. Engaging and using the chin alone, while workable, could possibly cause jaw problems.

When knob 76 is rotated, displacement upwardly of the chin-mastoid piece 56 and/or the cheek or jaw piece 57 is enabled with respect to shoulder assembly 54 because of an incline of the support track 62, and of the alignment maintained in the support bracket 58. The support bracket 58 is schematically shown at 0° for purposes of clarity. Each of rods 64 and 68 are secured between alignment pin and an anchoring point on shoulder assembly 54. An air or other cylinder can be associated with rods 64 and 68 to act as a dampening means during the manual adjustments.

Figure 12:
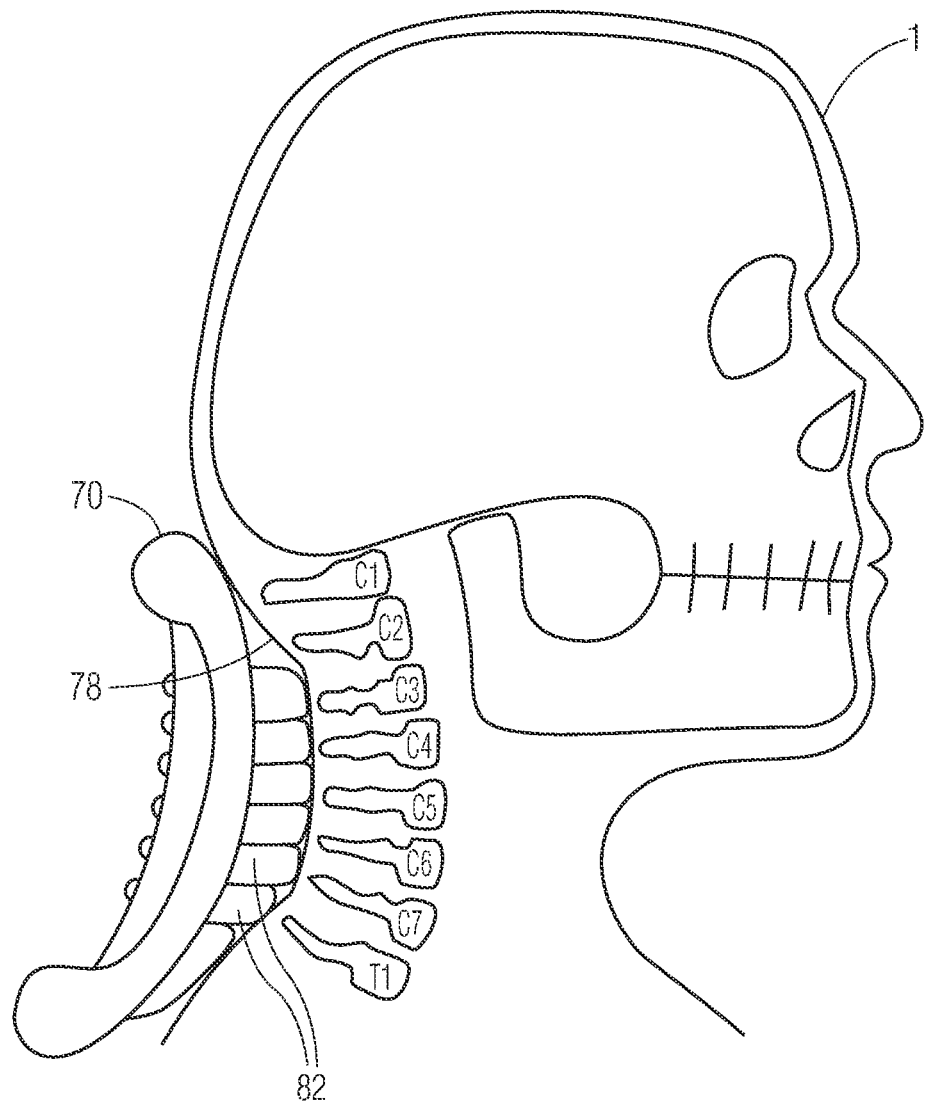
FIGS. 12 and 12A are side schematic views illustrating use of the lordosis correction assembly sown in FIG. 8, acting in concert with other features of the correction collar to correct lordosis in the cervical and upper thoracic portions of the spine of the hypothetical wearer.
Figure 12A:
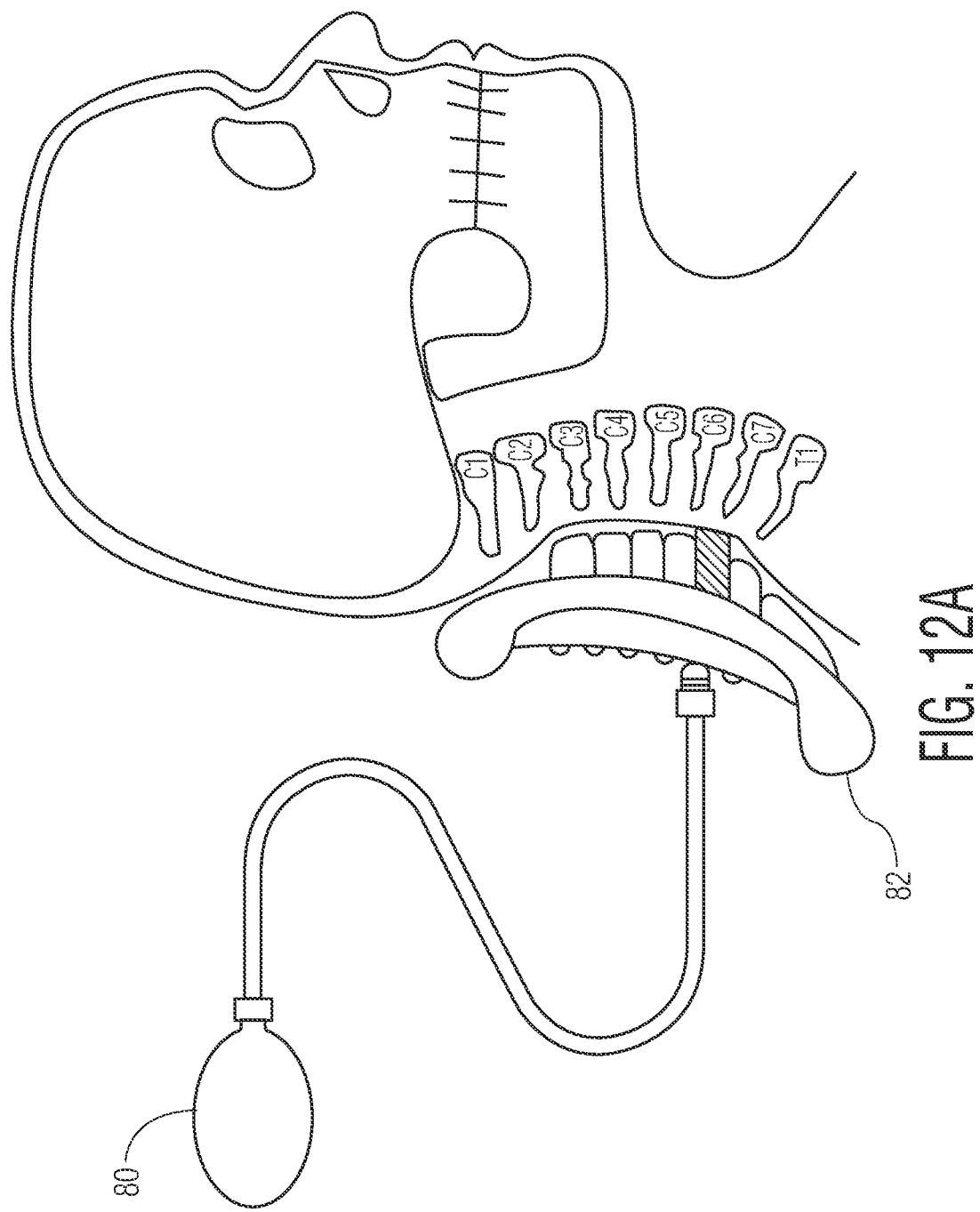
Figure 13:
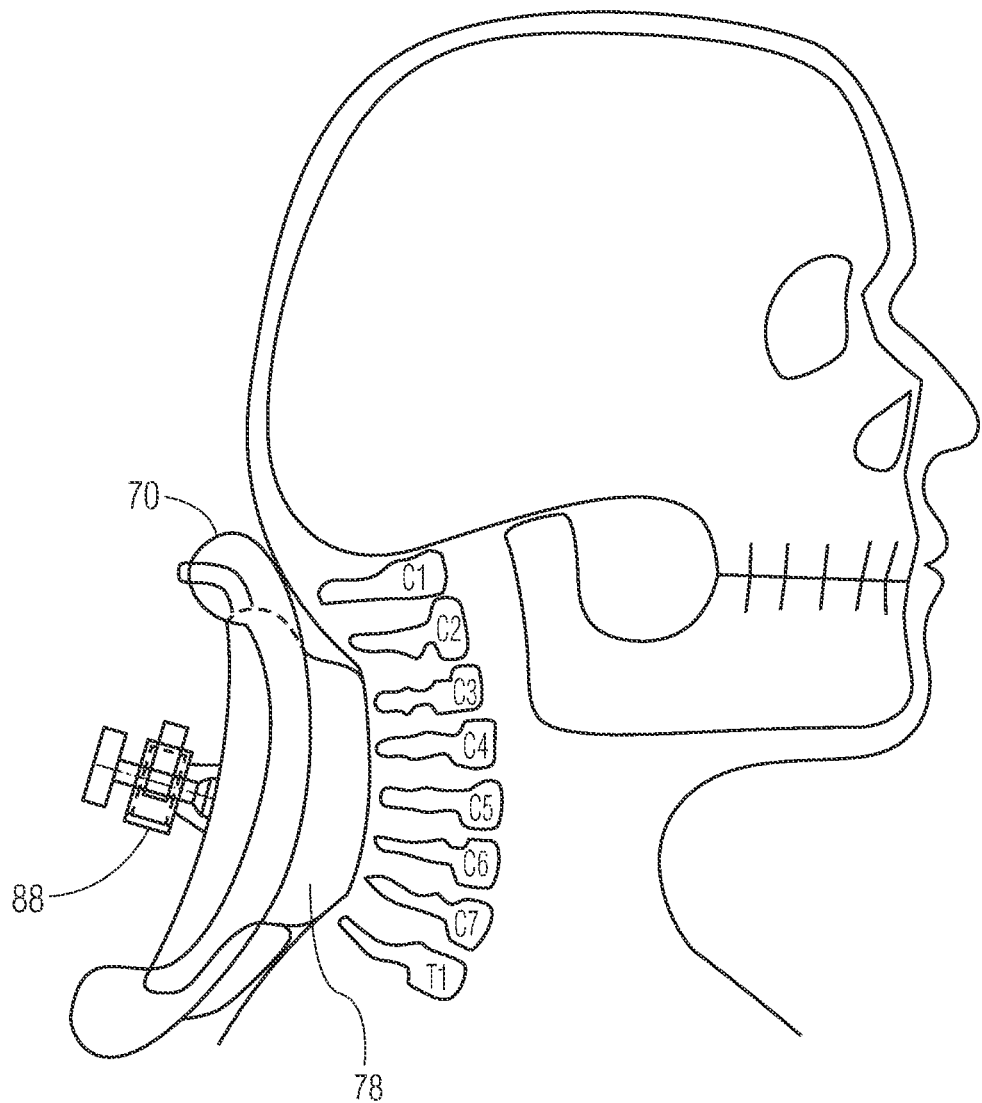
FIG. 13 is a side schematic view illustrating use of a third embodiment of a lordosis correction assembly in concert with other features of the invention to correct lordosis in the cervical and upper thoracic portions of the of the spine of a hypothetical wearer, the lordosis correction assembly having a tensioning mechanism.

The present apparatus as further seen in FIGS. 8, 12 and 13 can also be associated with a lordosis correction assembly 70, which as is seen in these schematic views can comprise a user inflatable portion and an underlying pressure contact surface 78. The lordosis correction assembly 70 is inflatable by a simple hand bulb as shown at (FIG. 12A). The purpose of this assembly is to correct the lordosis curve upon the selected displaced position of the chin-mastoid piece 56 and/or the cheek or jaw piece 57 being achieved. The precise form of the lordosis correction surface 78 may be in accord with the devices and curvature configurations discussed at length in the present Dellanno, U.S. Pat. Nos. 5,181,763, 5,290,091 and 5,580,124, among others, the disclosures of which are incorporated by reference herein.

The correction surface 78 can comprise a plurality of separate adjoining pads 82. These can be of a foam or a similar material, or as shown in FIGS. 12 and 12A, and can be each a separate inflatable unit or cell. This enables increased pressure to be brought selecting against specified vertebrae. Thus separate input ports such as 84 and 86, etc. can be connected to an air pressure source to expand the connected inflatable unit against a particular vertebra. FIG. 12A shows such a connection being made in order to advance the expanded pad 82a against the C7 vertebra. Interconnection between input port 84 and pads 82 is made by a tube and suitable valving.

Figure 14:
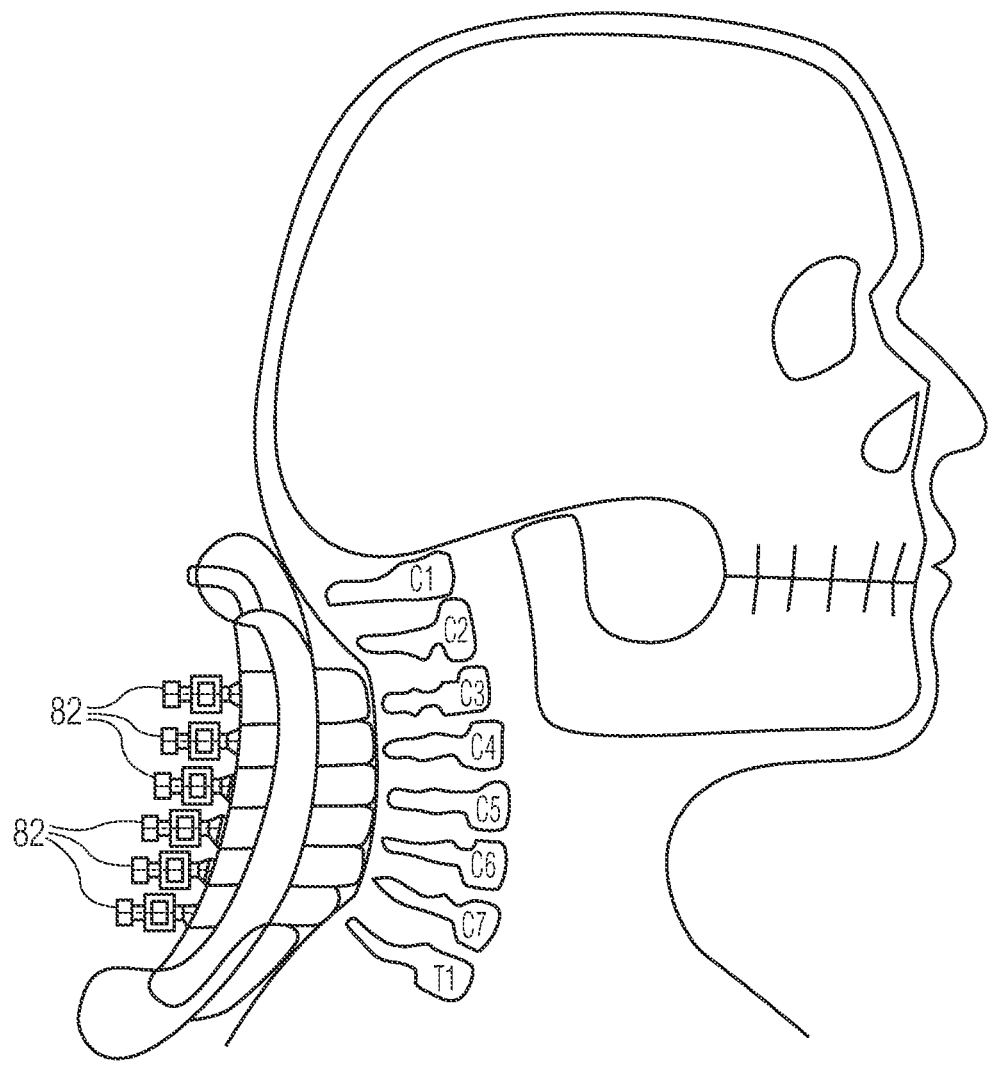
FIG. 14 is a side schematic view illustrating use of a fourth embodiment of a lordosis correction assembly in concert with other features of the invention to correct lordosis in the cervical and upper thoracic portions of the spine of a hypothetical wearer, the lordosis correction assembly having a plurality of tensioning mechanisms.
Figure 15A:
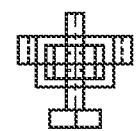
FIGS. 15A, 15B, and 15C show top, front and side schematic views of the tensioning mechanism used in FIGS. 13 and 14.
Figure 15B:
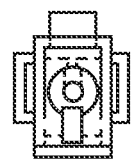
Figure 15C:
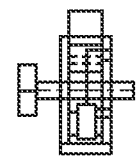
Figure 16:
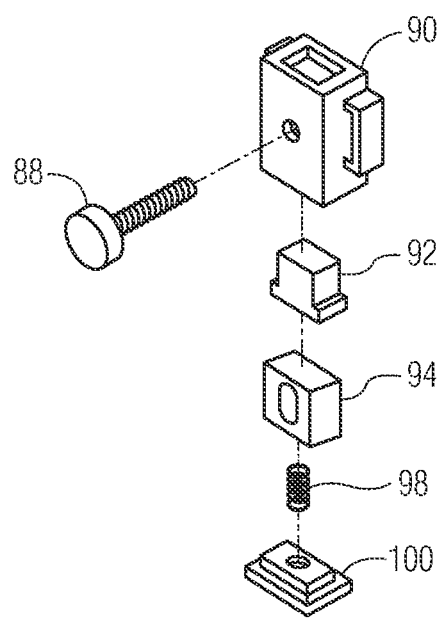
FIG. 16 is an exploded view of the tensioning mechanism of FIGS. 15A, 15B and 15C.

As also mentioned, pads 82 can be non-inflatable units formed of rigid or soft foams or other materials. In such instances the pads can be selectively advanced against desired vertebrae by simple mechanical arrangements. The distal ends of the pads 82 (remote from the patient) can be covered by hard plates, which are biased toward the patient by an adjustable threaded member 88 extending through housing 90 to a point at the rear of the lordosis correction assembly 70. As shown in FIGS. 13 and 14, a plurality of adjustable advancing means 92 are associated with individual foam pads 82. A suitable construction for means 92 is shown in FIGS. 15A, 158, I 5C and 16. The threaded member 88 passes through a mating half nut 94 which is in contact with button 96 and retained by spring 98 and end cap 100 which bears against the assembly and which by its rotation can enable the adjustment.

The pads 82 can also be inflatable, but instead of directly bearing against the user's spine, can drive separate but contacting pads against the spine, where such separate pads are comprised of foams or other materials.

A key aspect of the present invention is that means are provided which interconnect the chin-mastoid piece and/or the cheek or jaw piece to the shoulder collar assembly; such that these means are manually and incrementally adjustable so that the chin-mastoid piece and/or the cheek or jaw piece may simultaneously be moved in two explicit directions, one of these being in an anterior/posterior direction, i.e. along the Z axis, and also in a vertical direction with respect to the shoulder collar assembly. Furthermore these two types of simultaneous movement are such that the displacement along the vertical direction is proportional to the incremental simultaneous displacement along the Z axis. The functioning of these principles of the invention are best appreciated by viewing FIG. 21 which very graphically illustrates (at top portion of the Figure) the changes in the configuration (at A, B, and C) of the head and spine and the changes in the spinal lordosis which occur as the foregoing step-wise and time-wise adjustments are effected (via knob) in the positioning of the chin-mastoid piece and/or the cheek or jaw piece relative to the shoulder collar assembly.

The present invention thus seeks to treat the medical condition now known as Cervical Kyphosis/Forward Head Posture Syndrome. In order to correct this crippling condition, the patient's neck curve must be supported at the precise vertebrae that are causing the reversal of the neck curve while simultaneously repositioning the head rearward to align over the shoulders. This latter movement is a rearward translational movement and not the rotational movement as can be seen in the cited prior art.

Returning to FIG. 1, the collar assembly 10 of the present invention is shown for use in positioning the head of a wearer to a desired condition. The collar assembly 10 is used in a similar manner to collar 52 previously discussed. Collar assembly 10 comprises a first assembly member 102 that forms a base support on which is attached a movable second assembly member 104. The second assembly member 104 is adapted to be removed from and move relative to the first assembly member 104 to use the collar assembly 10.

Figure 17:
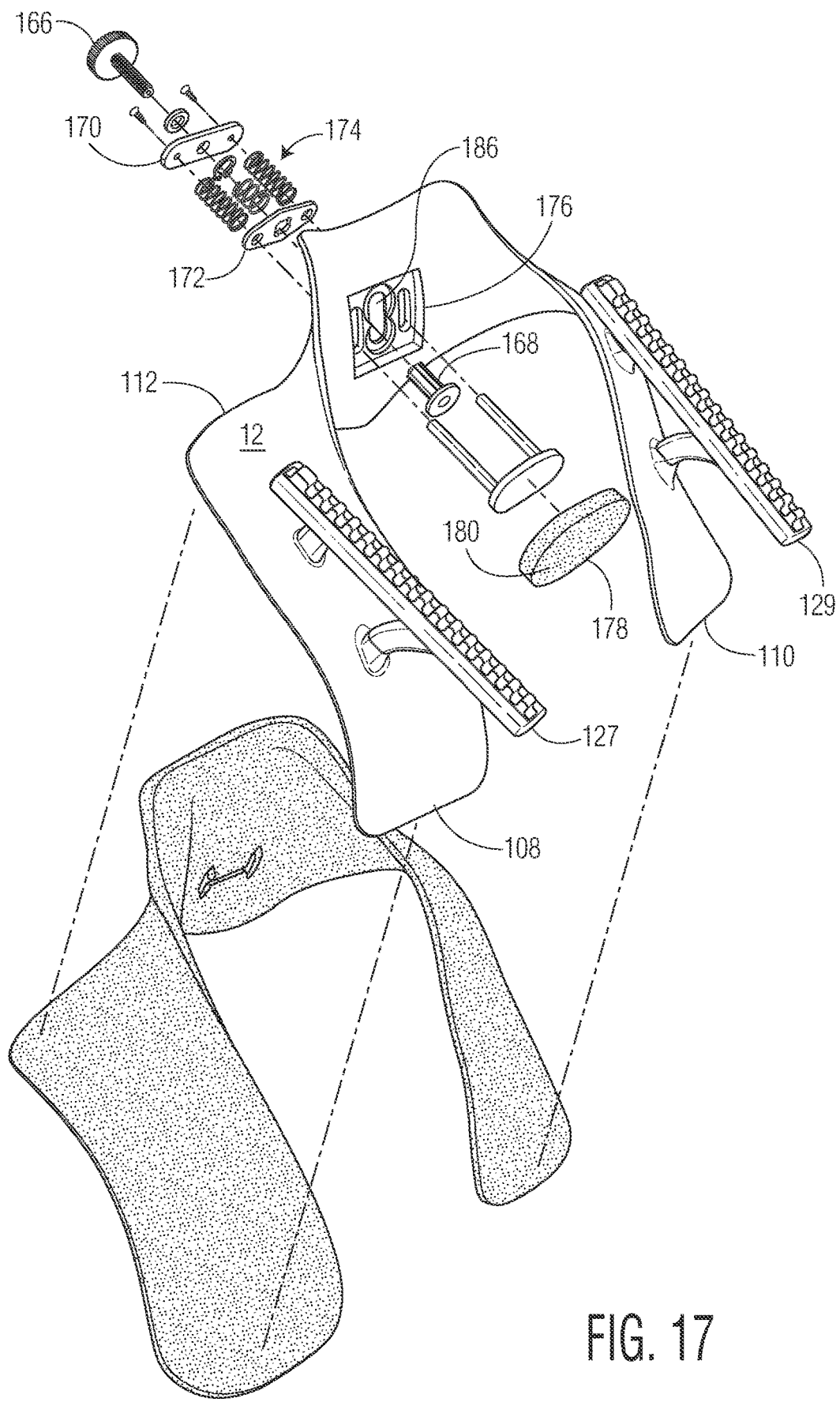
FIG. 17 is an exploded perspective view of the components of the first assembly of FIG. 1, illustrating the components of the first assembly and the lordosis correction assembly.

As shown in FIGS. 1 and 17, the first assembly member 102 comprises a shoulder pad 106 that is shaped or fit on the shoulders of and around the neck portion of the wearer. The first assembly member 102 is preferably made of a relatively hard, but relatively flexible and durable polymer such as polypropylene, polyethylene or nylon. Preferably some form of plastic is used for most of the components of the collar assembly 10 to reduce weight and provide a device that is durable when used over a period of time.

The shoulder pad 106 has two arms, namely the first are 108 and a second arm 110, that are joined together at the back 112 from which a neck support 114 extends away from the two arms 108 and 110. Preferably, the two arms 108 and 110 are made of nylon using an injection molding process that incorporates the back 112, which is made of the same material. To cushion the mounting and use of the shoulder pad 106, the collar assembly 10 has durable, but soft cushion material member 116 that is attached to the surfaces of the first assembly member that will engage the user. The cushion material member 116 is preferably a foam laminate, which may include suede, or other shock absorbing and cushioning material that is comfortable for the user to wear. Faux suede material is preferred that is secured to the bad using an epoxy or industrial grade glue or other securing means known in the art. Similar individual engaging, but comfortable material is also applied to the cheeks and chin portion.

On opposite sides of the shoulder pad 106 are a first adjustment assembly 118 and a second adjustment assembly 120, which are positioned in spaced relation relative to each other along an imaginary longitudinal axis extending medial of the collar assembly Because adjustment assemblies 118 and 120 are mirror images of one another, adjustment assembly 118 will be described as illustrative of adjustment assembly 120.

Adjustment assembly 118 includes a first housing or adjustment member 130 contains a first movement means 122 and an integrated first tower assembly 136 that work cooperatively to enable the position and condition of a first side of second assembly member 104 to move relative to the first assembly member 102. The movement means 122 includes a track 126 that has teeth for controlling the step movement of the adjustment assembly 118 relative to the longitudinal axis 127 of the track 126 that extends along line parallel to the Z-axis of the collar assembly 10. Rotatable knob 20 used to adjust the position of adjustment member 130 and second assembly 104 along the track 126, Rotatable knob 20 can be turned clockwise or counterclockwise to operate pinion gear 24 to control the stepwise movement of the adjustment member 130 along the track 126. The adjustment member 130 extends away from the track 126 when it is mounted. The adjustment member 130 includes thee tower assembly 134 that is adapted to move in a periscope manner from a lower condition to an upper condition, relative to the long axis of the adjustment member 130.

On the opposite side of the collar assembly 10 there is the second adjustment assembly 120 which includes a second housing or adjustment member 132 contains a second movement means 124 and an integrated second tower assembly 136 that work cooperatively to enable the position and condition of a second side of second assembly 104 to move relative to the first assembly member 102. The movement means 124 includes a track 128 that has teeth for controlling the step movement of the second side of second adjustment assembly 120. The position of the first adjustment assembly 118 and the second adjustment assembly 120 can be moved when the user operates movement means 122 and movement means 124 in separately or in coordination with each other so that their respective adjustment assemblies 118 and 120 move along a line parallel to longitudinal axes 127 and 129 of their respective tracks. The operation of the movement means 122 and movement means 124 will cause tower assemblies 134 and 136 to also move toward the rear or away from the neck support 114 of the shoulder portion pad 106 of the collar assembly 10.

Figure 18:
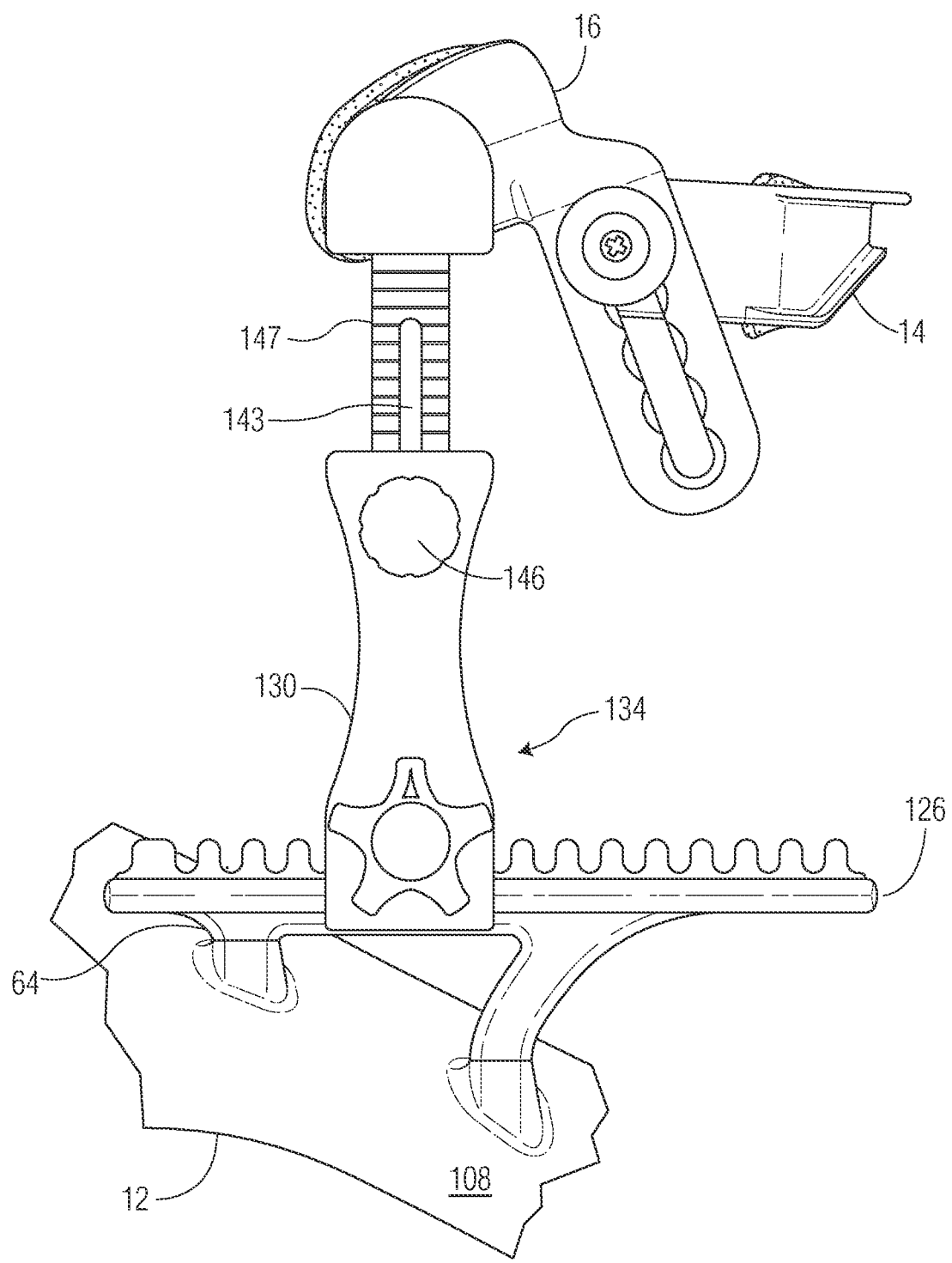
FIG. 18 is an isolated cutaway side view of the first side of components of the first and second assembles shown in FIG. 1, the second assembly being in a first condition.
Figure 19:
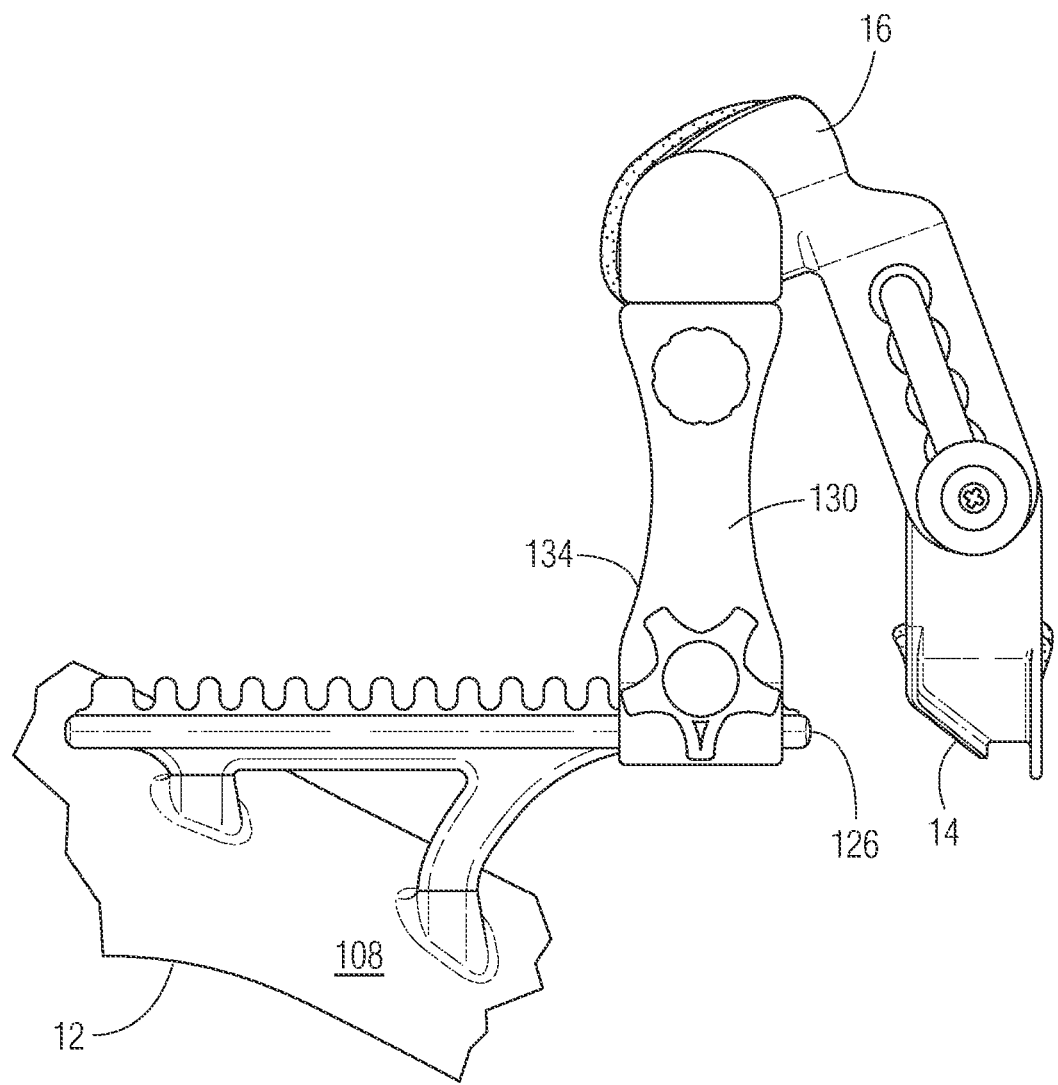
FIG. 19 is an isolated cutaway side view of the first side of components of the first and second assemblies shown in FIG. 1, the second assembly being in a second condition.

Because tower assemblies 134 and 136 are mirror images of one another, the description of tower assembly 134 will be exemplary of the description of tower assembly 136. As illustrated in FIGS. 18 and 19, first tower assembly 134 has a lower condition (FIG. 18) and an upper condition (FIG. 19), based on movement of a first positioning assembly 138 that is configured and adapted to move toward and away from the upper portion of the tower assembly 134, which is in a direction toward the bottom of the paper and toward the top of the paper. A rotatable locking knob 140 that has a threaded end and a portion (each not shown) that projects through and slidably moves within a slot 143 within positioning member 147 that is configured and adapted to slide within tower assembly 134. The rotatable locking knob 140 is used to lock in the desired position of the positioning bar or member 147, relative to a series of segments 151, which in turn locks in the position of the first positioning assembly member 138 at a given segment.

The first positioning assembly 138 has a bracket arms 144 that is joined at its proximal end to the first cheek or jaw piece 16 at one end. A second end of the first cheek or jaw piece 16 is rotatably connected to the first positioning assembly 138 by a pivot pin 156. The bracket arm 144 is joined at its distal end to the first side of chin-mastoid piece 14, which is operatively connection thereto by an alignment pin 152, to allow the position of the chin mastoid piece 14 to be adjusted by sliding alignment pin 152 within track 148.

Track 148 has a series of openings 150 formed within the interior of bracket arm 144 that further define the slot to facilitate stepped and controlled movement of the chin mastoid piece 14, so that the piece can be adjusted by sliding the locking pin 152 and securing it in place.

It should be understood that the second tower assembly 136, similar to the first tower assembly 134, has a lower condition and an upper condition, which is based on movement of a second positioning assembly 139 that is configured and adapted to move toward and away from the upper portion of the tower assembly 136. A rotatable locking knob 142 that has a threaded end and a portion (each not shown) that projects through and slidably moves within a slot 144 within positioning member 149 that is configured and adapted to slide within tower assembly 136. The rotatable locking knob 142 is used to lock in the desired position of the positioning member 149, relative to a series of segments 153, which in turn locks in the position of the second positioning assembly member 139 at a given segment. The second positioning assembly is joined to one side of the second cheek or jaw piece by a pivot pin 158 and is joined to the another side of the second cheek or jaw piece to an arm 146, which contains track 150 that is configured and adapted to receive alignment locking pin 154 that slides within track 150. Track 150 has a series of openings 162 formed within the interior of bracket arm 146 that further define the slot 145 to facilitate stepped and controlled movement of the chin mastoid piece 14, so that the piece can be adjusted by sliding the locking pin 154 and securing it in place.

The chin mastoid piece 14 and the check or jaw pieces 16 and 18 are used to engaging and positioning the head of the wearer of the collar assembly 10. The position of the chin mastoid piece 14 and the cheek or jaw pieces 16 and 18 are adjusted by operating adjustment assembly 118 and adjustment assembly 120 relative to shoulder assembly 12 so as to adjust the position of the collar assembly 10. The collar assembly can be adjusted to be positioned to a desired position on the wearer's neck and cervical spine.

As shown in FIGS. 1, 3, 5, 6, and 17, the collar assembly 10 includes a lordosis correction fulcrum assembly 164. The fulcrum assembly 164 includes a spring loaded thumb screw 166 that is operatively joined to a cap 168 and plates 170 and 172 that are assembled with springs 130 intermediate their inner facing sides. The plates 170 and 172 joined to a fulcrum lock keyed mechanism 176 that is use to move a padded adjustment member 178 which is shaped to engage the portion of the neck and thereby move a certain portion of the vertebra of the cervical spine into a desired position. By turning the thumb screw, pad 180 will urge against the cervical vertebra, preferably the C2 to C7 vertebra, to return the cervical vertebra to close to its normal anatomical position, as illustrated in FIG. 21. The thumb screw 166 will be held in place by the threads and the locked position of the fulcrum lock key mechanism to reduce the lateral movement of the pad 180 when the collar assembly 10 is mounted on the wearer to adjust the cervical vertebra. Preferably, during use, the thumb screw 166 can be adjusted such that the position of the pad can move along the longitudinal axis, parallel to the longitudinal Z-axis of the collar assembly 10 or the longitudinal axis 127 and 128 of tracks 126 and 128, respectively. The movement of the thumb screw 166 is controlled by turning it clockwise to urge the pad 180 toward the spine or counterclockwise to recoil the pad 180 away from the spine.

Figure 20:
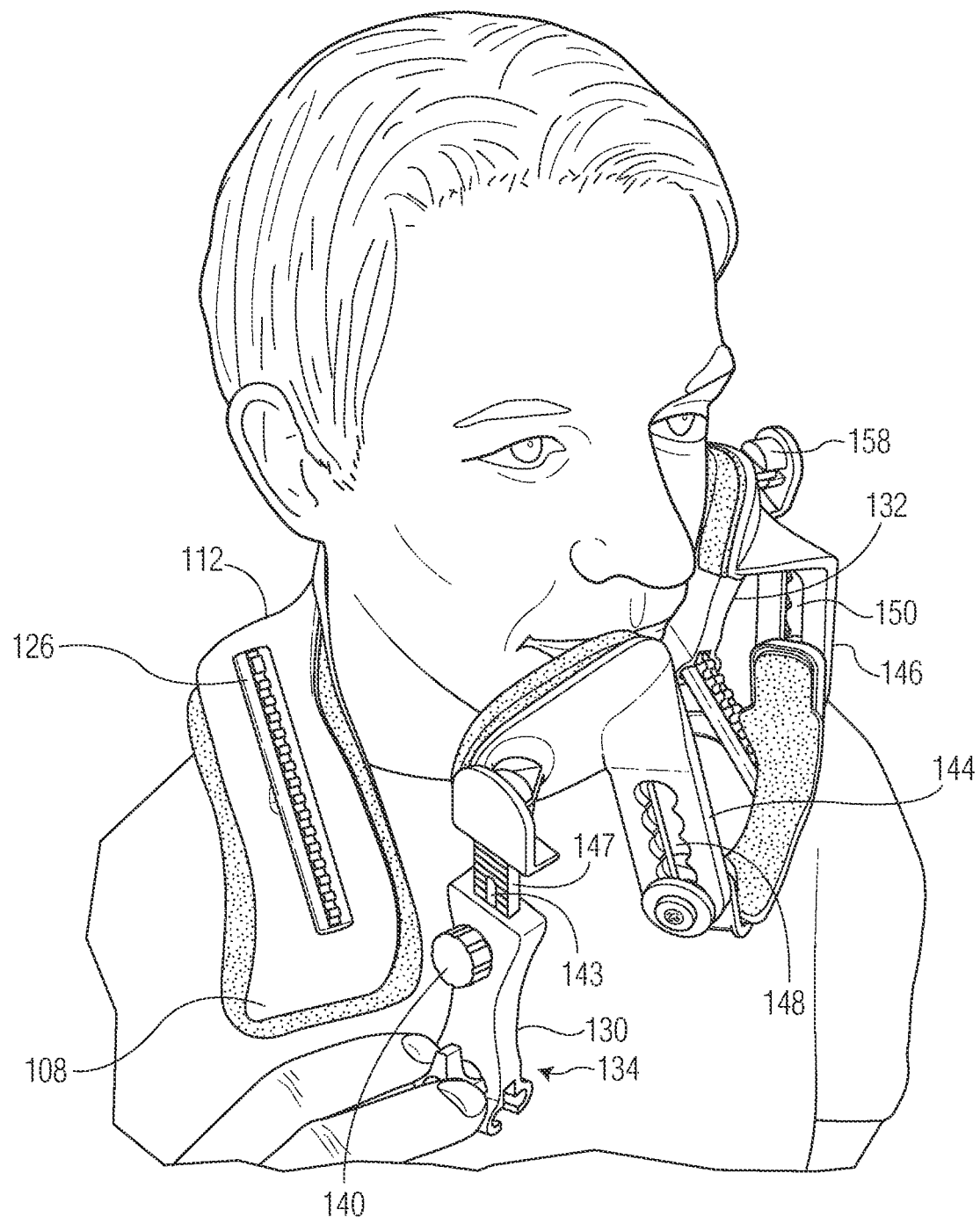
FIG. 20 is a perspective view illustrating one method of mounting the forward head posture correction collar shown in FIG. 1 to the head and body of the hypothetical wearer.

FIGS. 1 and 20, the assembly and mounting of the collar assembly 10. In use, the physician will perform an x-ray of the individual patient and conduct an exam to determine the degree of the translation of the cervical spine from its normal anatomical position. The physician will consider the individual's history, causes of the deformity, physical activities, and the likely cause of the changes to the cervical spine.

On both sides, slide the open ends of the shoulder arms 108 and 110 using gentle pressure to help engage the collar assembly 10 on the head of the individual. Then, the knobs 20 and 22 on both sides of the collar assembly 10 so that the adjustment assembly 120 and adjustment assembly 122 will engage track 126 and track 128, respectively. The tower assemblies 134 and 136 will move along tracks 126 and 128, respectively, by operating knobs 20 and 22.

Leave the fulcrum assembly 164 in a default lower position 182 (See FIG. 5) or an upper position 184. To adjust, depress the thumb screw 166 while compressing springs 174 and slide fulcrum up or down in the slots 186 of the fulcrum lock key mechanism 176. Turn thumb screw 166 until the padded adjustment member 178 to desired position. It should be noted that the thumb screw 166 can be adjusted as described in this step while patient is wearing collar if desired. Both adjustment assemblies 118 and 120 should be in a full forward position and engaged with track. The chin mastoid piece 14 can be adjusted so that it will engage the bottom portion of the chin of the individual. As shown in FIGS. 18 and 19, the pivot pins 156 and 158, respectively, can be used to position the chin mastoid piece 16. The collar assembly 10 can be pulled over the head from back and top, avoiding ears. Then, the knobs 20 and 24 can be adjusted, along with positioning the cheek or jaw pieces 16 and 18 evenly so that they rest on cheek bones. Re-tighten knobs 140 and 140 to keep the chin mastoid a14 and cheek and jaw pieces 16 and 18 in place. The chin mastoid piece 14 can be rotated about pins 156 and 158 as needed by pulling spring buttons 188 and 200 out and sliding the pivot pins 156 and 158 up or down within their respective tracks 148 and 150, making sure the chin rest is positioned comfortably below chin.

For example, since the FHP is a position that produces damaging structural stress on the entire spine it is reasonable to apply the collar in post-operative spine surgery patients. This applies to cervical, thoracic, or lumbo-pelvic post-surgical procedures. This allows healing of the spinal joints without the damaging shear and moment mechanical stresses produced by the forward head posture position. For the above reasons the collar may also be used in post-traumatic situations from car accidents or sports injuries, etc. Therefore hospitals and EMT personnel will desirably employ its use. The lordosis correction assembly can also be used with conventional cervical collars where forward head posture correction may be difficult, i.e., with older patients where fusion of spinal joints has advanced to a point where minimal movement is possible. These conditions will still benefit from some mild lordosis support. This will reduce some of the mechanical strain and pain in these patients.

The progressive improvement of the cervical lordosis requires precise support to the offending misaligned vertebrae. In the examples cited, the vertebra is C5. As illustrated in FIG. 21, typically as treatment progresses from A to B in approximately one month, B shows the head moved in the −Z direction to align over the shoulders. There is no extension or flexion movement required. The neck in B moves in a +Z translation or forward direction. A full contoured support would not be sufficient because it spreads the support over a large area, C1-C7. Finally, in FIG. 21 at C, the neck curve has been restored to normal and the forward head posture has been repositioned over the shoulders by the collar's upward angled −Z directional movement. These motions and intended clinical correction of the Forward Head Posture and Cervical Kyphosis are not discussed in the prior art and could not be achieved by the prior art because there must be simultaneous correction of both forward head posture and a precise support to the misaligned cervical vertebrae in order to change the cervical kyphosis into a cervical lordosis. This treatment will prevent cervical arthritis and cervical disc degeneration and painful neck misalignments.

While the present invention has been set forth in terms of specific embodiments thereof, the instant disclosure is such that numerous variations upon the invention are now enabled to those skilled in the art, which variations yet reside within the scope of the present teachings. Accordingly, the invention is to be broadly construed and limited only by the scope and spirit of the claims now appended hereto. The description of the material used applies to all embodiments described herein, it be understood that the invention covers equivalent material known in the medial and manufacturing arts, which are acceptable to governmental agencies, such as the United States Food and Drug Administration. The embodiments shown are exemplary and it is contemplated that other equivalent forms can be used within the scope of the objects of the invention.

The invention claimed is:

1. An adjustable forward head posture assembly configured for positioning and translating the head of a wearer along a Z-axis direction of the adjustable forward head posture assembly to a desired position, the adjustable forward head posture assembly comprising:
   a first assembly adapted to be removably mounted to the wearer, the first assembly having a shoulder pad that is shaped and dimensioned to mount onto and wrap around shoulder and neck portions of the wearer, the shoulder pad having a first arm and a second arm that are joined together at a neck portion,
   a second assembly having a chin-mastoid piece that is configured to adjustably engage a portion of the chin of the wearer, wherein the chin-mastoid piece has a first side that is adjustably joined to a separate first cheek piece that is configured to engage a first upper cheek portion of the head of the wearer and the chin-mastoid piece has a second side that is adjustably joined to a separate second cheek piece that is configured to adjustably engage a second upper cheek portion of the head of the wearer, wherein the first cheek piece and the second cheek piece are adjustably joined to the sides of the chin-mastoid piece by a pair of arms having a slot and locking pins operatively and slidably connected thereto,
   a first adjustment assembly to interconnect the first cheek piece to the first assembly, the first adjustment assembly having a track and pinion mechanism that is configured to enable the first side of the second assembly to move relative to the first assembly and a positioning assembly having a first slideable positioning bar that is configured to enable the first cheek piece be moved to a desired position relative to the head of the wearer,
   a second adjustment assembly to interconnect the second cheek piece to the first assembly, the second adjustment assembly having a track and pinion mechanism that is configured to enable the second side of the second assembly to move relative to the first assembly and a positioning assembly having a second slideable positioning bar that is configured to enable the second cheek piece to be moved to a desired position relative to the head of the wearer, and a fulcrum assembly operatively connected to the first assembly that is configured and adapted to move along a line parallel to the Z-axis, wherein the fulcrum assembly includes an adjustable spring loaded screw movably formed within the shoulder pad and joined to a cervical adjustment pad that is configured to engage cervical areas of the neck of the wearer, whereby actuating the fulcrum assembly causes the cervical adjustment pad to translate the head of the wearer to the desired position.

2. The adjustable forward head posture assembly according to claim 1, wherein a track of the first adjustment assembly is secured to the first arm of the first assembly and a track of the second adjustment assembly is secured to the second arm of the first assembly.

3. The adjustable forward head posture assembly according to claim 2, wherein the adjustable spring loaded screw has a series of threads to permit stepwise translation of the cervical adjustment pad in a line parallel to the Z-axis.

4. The adjustable forward head posture assembly according to claim 1, wherein the track and pinion mechanism of the first adjustment assembly is operately joined to a first rotatable knob and the track and pinion mechanism of the second adjustment assembly is joined to a second rotatable knob.

5. The adjustable forward head posture assembly according to claim 4, wherein a track of the first adjustment assembly further comprises a plurality of teeth to engage the pinion for stepwise movement of the second assembly relative to the first assembly.

6. The adjustable forward head posture assembly according to claim 1, wherein the first cheek piece is pivotably attached to the first adjustment assembly by a first pivot pin and wherein the second cheek piece is pivotably attached to the second adjustment assembly by a second pivot pin, whereby the first cheek piece and the second cheek piece are configured to swing relative to the first assembly.

7. The adjustable forward head posture assembly according to claim 1, wherein the chin-mastoid piece is configured to rotate to engage a portion of the chin of the wearer.

* * * * *